United States Patent [19]
Erickson et al.

[11] Patent Number: 5,178,173
[45] Date of Patent: Jan. 12, 1993

[54] ULTRASONIC CONTACT LENS CLEANING DEVICE

[75] Inventors: John J. Erickson; Drew D. Erickson, both of Kingston, N.Y.

[73] Assignee: Robert J. Pace, Saratoga, Calif.

[21] Appl. No.: 739,227

[22] Filed: Aug. 1, 1991

[51] Int. Cl.$^5$ .............................................. B08B 3/12
[52] U.S. Cl. ........................................ 134/184; 134/1; 134/901; 366/127
[58] Field of Search ................... 134/1, 184, 901; 366/127

[56] References Cited

U.S. PATENT DOCUMENTS

| | | | |
|---|---|---|---|
| 2,554,701 | 5/1951 | Hackett et al. | 134/1 X |
| 3,094,314 | 6/1963 | Kearney et al. | 366/127 X |
| 3,535,159 | 10/1970 | Shiro | 134/1 |
| 3,575,383 | 4/1971 | Coleman | 366/127 X |
| 3,720,402 | 3/1973 | Cummins et al. | 134/1 X |
| 3,871,395 | 3/1975 | Murry | 134/901 X |
| 4,382,824 | 5/1983 | Halleck | 134/1 |
| 4,537,511 | 8/1985 | Frei | 366/127 |
| 4,556,467 | 12/1985 | Kuhn et al. | 134/1 X |
| 4,691,725 | 9/1987 | Parisi | 134/901 X |
| 4,710,233 | 12/1987 | Hohmann et al. | 134/184 X |
| 4,836,684 | 6/1989 | Javorik et al. | 134/1 X |
| 4,852,592 | 8/1989 | DiGangi et al. | 134/901 X |
| 4,870,982 | 10/1989 | Liu | 366/127 X |
| 5,071,776 | 12/1991 | Matsushita et al. | 134/1 X |

Primary Examiner—Philip R. Coe
Attorney, Agent, or Firm—Daniel Jay Tick

[57] ABSTRACT

An ultrasonic contact lens cleaning device has a housing with a hemispherical cover hingedly affixed to it. A container for a lens cleaning solution is mounted in the housing. An acoustic resonant structure in the housing is coupled to the container. The structure has piezoelectric components. A frequency modulated power circuit in the housing is electrically connected to and drives the acoustic resonant structure and provides a controlled level of ultrasonic cleaning energy.

13 Claims, 4 Drawing Sheets

ULTRASONIC CONTACT LENS CLEANING DEVICE

BACKGROUND OF THE INVENTION

The present invention relates to an ultrasonic contact lens cleaning device.

Contact lenses must be cleaned and sanitized on a daily or flexible extended wear schedule with special care in order to preserve the optical quality of the lenses and the good health of the wearer. In a recommended cleaning technique, the fingers and the palm of the hand are used to rub deposits from the lens, which thus may scratch or otherwise harm the surface of the lens.

Presently available devices for assisting in cleaning and disinfection of contact lenses include the mechanical agitation of baskets holding a pair of lenses in a cleaning solution manually or by electric motor. Another known device utilizes manual mechanical agitation combined with standing wave vibrations of the cleaning solution to provide for cleaning of the lenses. These devices are ineffective in removing some of the contact lens deposits including cosmetics and protein which adhere to the surface of the lenses. Other previous ultrasonic devices utilize a single piezoelectric crystal bonded to the bottom of one or more liquid holding containers, which produce a lateral resonance vibration mode. These devices also have been ineffective in removing contact lens deposits, as discussed.

The principal object of the invention is to provide an ultrasonic contact lens cleaning device of simple structure which is inexpensive in manufacture and operation.

An object of the invention is to provide an ultrasonic contact lens cleaning device which functions efficiently, effectively and reliably to clean and disinfect contact lenses.

Another object of the invention is to provide an ultrasonic contact lens cleaning device which is used with facility and convenience to thoroughly clean contact lenses with minimum handling and without optical degradation.

Still another object of the invention is to provide an ultrasonic contact lens cleaning device which is easy to use and does not scratch or harm any surface of the lenses cleaned.

BRIEF SUMMARY OF THE INVENTION

In accordance with the invention, an ultrasonic cleaning device for cleaning an item having surfaces desired to be kept free of scratching and the like, comprises a liquid holding container having a cleaning solution therein. Acoustic resonant structural means having piezoelectric components is operatively coupled to the container. Frequency modulated power means is electrically connected to and drives the acoustic resonant structural means and provides a controlled level of ultrasonic cleaning energy.

The acoustic resonant structural means comprises a pair of piezoelectric crystals, a pair of metal end sections, the crystals being sandwiched between the end sections, and means holding the crystals and the end sections in axial relation.

The acoustic resonant structural means is adhered to the container.

The container comprises plastic material.

The container has a lid and item holding means affixed to the lid for holding an item in a cleaning solution in the container and permitting free flow of the solution on the item.

The container comprises plastic material and has a plastic lid and item holding means affixed to the lid for holding a plurality of items separately from each other in a cleaning solution in the container and permitting free flow of the solution on each of the items.

The frequency modulated power means provides drive electrical energy at which the acoustic resonant structural means is driven and the drive energy has a frequency which is continually varied at 120 Hertz to compensate for variations in solution depth in the container.

The drive energy provides high power ultrasonic drive of predetermined duration for cleaning and lower power ultrasonic drive of a duration a multiplicity of times of the predetermined duration for total operation.

In accordance with the invention, an ultrasonic contact lens cleaning device comprises a liquid holding container having a lens cleaning solution therein. Acoustic resonant structural means has piezoelectric components and is operatively coupled to the container. Frequency modulated power means is electrically connected to and drives the acoustic resonant structural means and provides a controlled level of ultrasonic cleaning energy.

The acoustic resonant structural means comprises a pair of piezoelectric crystals, a pair of metal end sections, the crystals being sandwiched between the end sections, and means holding the crystals and the end sections in axial relation.

The acoustic resonant structural means is adhered to the container.

The container comprises plastic material.

The container has a lid and lens holding means affixed to the lid for holding a lens in a cleaning solution in the container and permitting free flow of the solution on the lens.

The container comprises plastic material and has a plastic lid and lens holding means affixed to the lid for holding a plurality of lenses separately from each other in a cleaning solution in the container and permitting free flow of the solution on each of the lenses.

The frequency modulated power means provides drive electrical energy at which the acoustic resonant structural means is driven and the drive energy has a frequency which is continually varied at 120 Hertz to compensate for variations in solution depth in the container.

The drive energy provides high power ultrasonic drive of predetermined duration for cleaning and lower power ultrasonic drive of a duration a multiplicity of times of the predetermined duration for total operation.

In accordance with the invention, an ultrasonic contact lens cleaning device comprises a housing, a hemispherical cover hingedly affixed to the housing and a container for lens cleaning solution mounted in the housing. Acoustic resonant structural means in the housing are coupled to the container. The structural means has piezoelectric components. Frequency modulated power means are in the housing and are electrically connected to and drive the acoustic resonant structural means and provide a controlled level of ultrasonic cleaning energy.

The container has a lid and lens holding means affixed to the lid for holding a plurality of lenses separately from each other in the cleaning solution in the container while permitting free flow of the solution on each of the lenses.

In accordance with the invention, an ultrasonic method of cleaning an item having surfaces desired to be kept free of scratching and the like comprises the steps of operatively coupling acoustic resonant structural means to a liquid holding container having a cleaning solution therein and driving the acoustic resonant structural means with frequency modulated electrical power to provide a controlled level of ultrasonic cleaning energy.

The electrical power has a frequency which is continually varied at 120 Hertz to compensate for variations in solution depth in the container.

BRIEF DESCRIPTION OF THE DRAWINGS

In order that the invention may be readily carried into effect, it will now be described with reference to the accompanying drawings, wherein.

DETAILED DESCRIPTION OF PREFERRED EMBODIMENT

Figure 1:
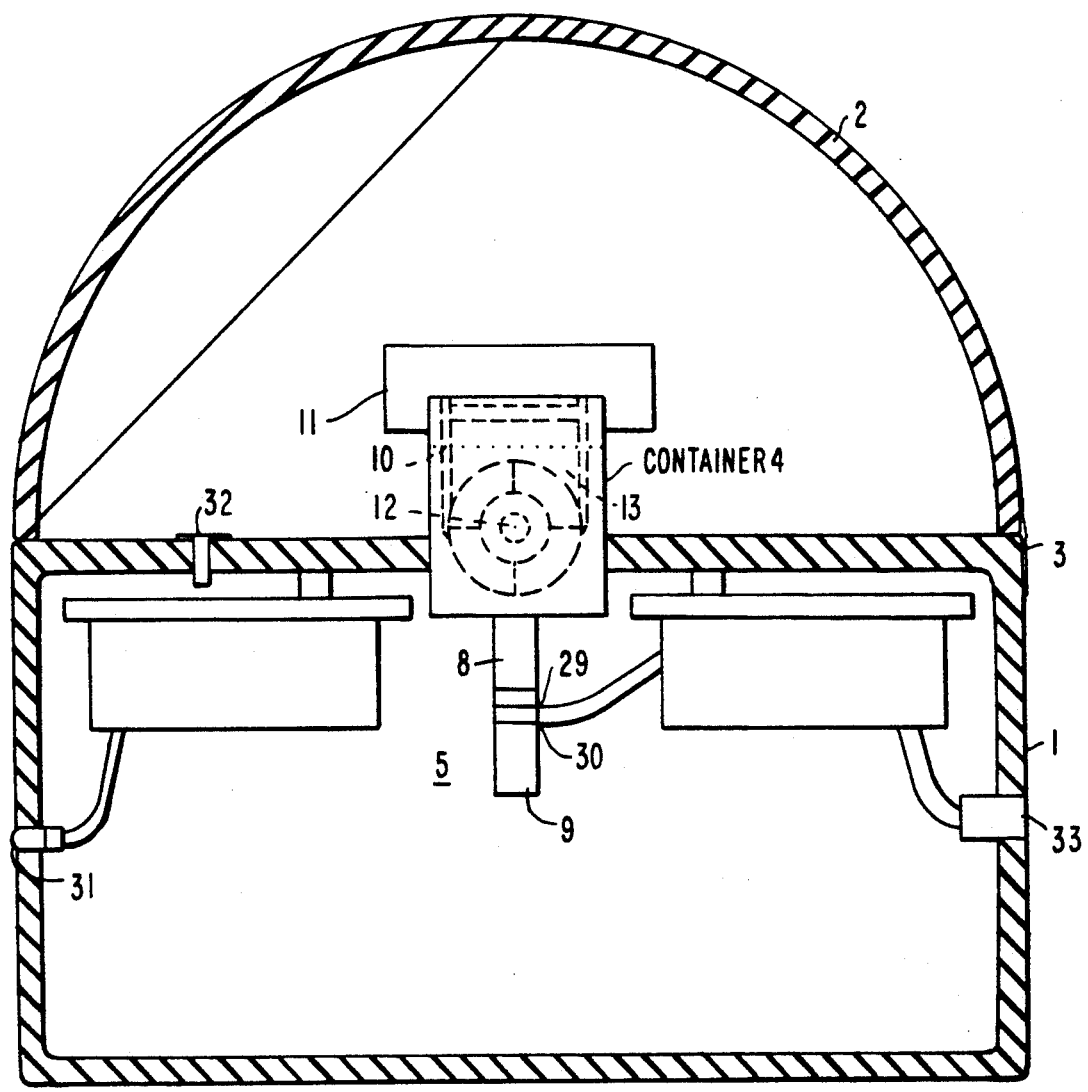
FIG. 1 is a view, partly a block diagram and partly in section, of an embodiment of the ultrasonic contact lens cleaning device of the invention.

The ultrasonic contact lens cleaning device of the invention comprises a housing 1 having a hemispherical cover 2 hingedly affixed to said housing, as shown in FIG. 1, via any suitable means such as, for example, hinge means 3. A container 4 for a lens cleaning solution of any suitable type is mounted in the housing 1 (FIG. 1).

Figure 2:
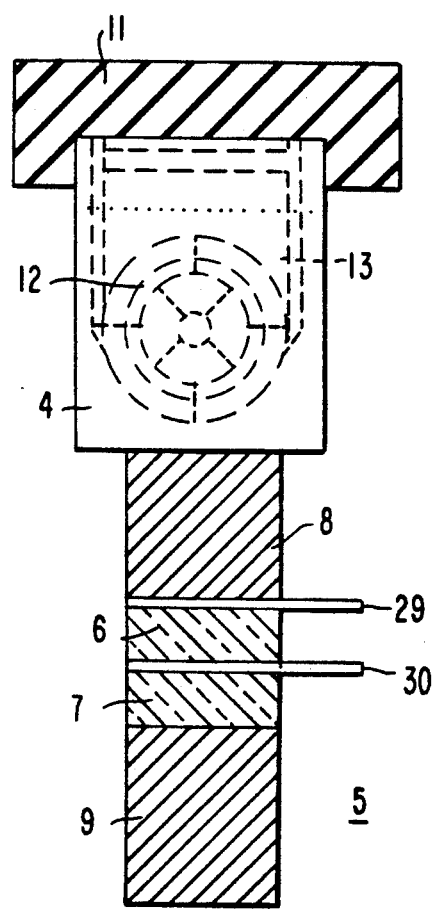
FIG. 2 is a sectional view of an embodiment of part of the ultrasonic contact lens cleaning device of the invention.

A acoustic resonant structure 5 (FIGS. 1 and 2) is provided in the housing 1 coupled to the container 4. The acoustic resonant structure 5 comprises a pair of piezoelectric crystals 6 and 7 of any suitable known type (FIG. 2) and a pair of metal end sections 8 and 9 (FIGS. 1 and 2). The crystals 6 and 7 are sandwiched between the end sections 8 and 9 and a compression bolt arrangement of any suitable known type holds said crystals and said end sections in axial relation. The sandwich structure may be bonded to the bottom of the container 4 by any suitable means such as, for example, a fast curing epoxy. The sandwich structure and a fixed level of cleaning solution, indicated by a broken line 10 in FIG. 1, form a resonant acoustic one wavelength path.

The container 4 may comprise plastic material of any suitable type and has a lid 11 which may also comprise plastic material of any suitable type (FIGS. 1 and 2). A lens holder 12 (FIGS. 1 and 2) is affixed to the lid 11 and holds a plurality of lenses separately, or spaced, or independently, from each other in a cleaning solution 13 of any suitable known type in the container 4. The lens holder 12 permits free flow of the cleaning solution 13 on each of the lenses held therein. The lens holder 12 preferably comprises a suitable FDA-approved plastic material and is hinged, or the like, so that it may be manually opened and closed.

Frequency modulated power means is electrically connected to and drives the acoustic resonant structure 5 and provides a controlled level of ultrasonic cleaning energy. The lens cleaning device of the invention utilized as an FDA-approved appropriate contact lens cleaning solution cleans contact lenses in less than three minutes without harm to the lenses.

If the level of applied energy is controlled to within ten to twelve watts and is applied for two minutes and then ultrasonic applied energy is lowered to five watts for an additional seven minutes, the lens can be both cleaned and disinfected and the temperature of a fresh cleaning solution starting at not more than 30° C. will not rise to more than 65° C. and the lens will not be harmed due to excess heat or cavitation. The synergistic effect of ultrasonic energy promotes disinfection within ten minutes. Popular two step FDA-approved cleaning solutions such as the Barnes Hind Soft Mate Concept 1 and Concept 2 can be employed for the recommended cycle time to completely clean and disinfect a pair of contact lenses for replacement on the eyes as rapidly as twenty minutes in the device of the invention. Any suitable known solution for cleaning and disinfecting hard or soft contact lens may be used with the present invention.

The frequency modulated power means provides drive electrical energy at which the acoustic resonant structure 5 is driven. The drive energy has a frequency which is continually varied at 120 Hertz to compensate for variations in the depth of the solution 13 in the container 4. The drive energy provides high power ultrasonic drive of predetermined duration for cleaning and lower power ultrasonic drive of a duration a multiplicity of times of the predetermined duration for total operation.

Figure 3:
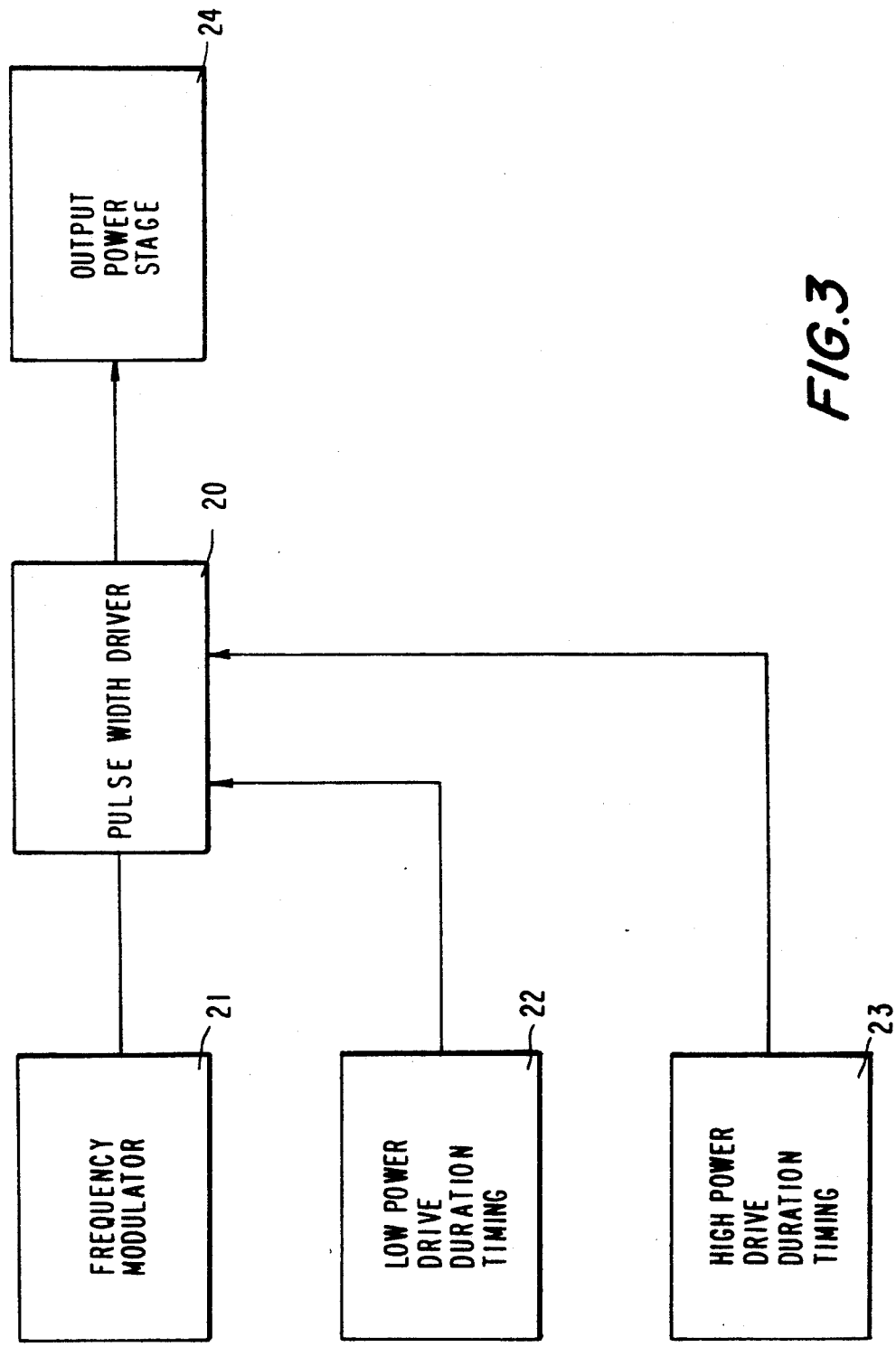
FIG. 3 is a block diagram of the power drive of the embodiment of FIG. 2.
Figure 4:
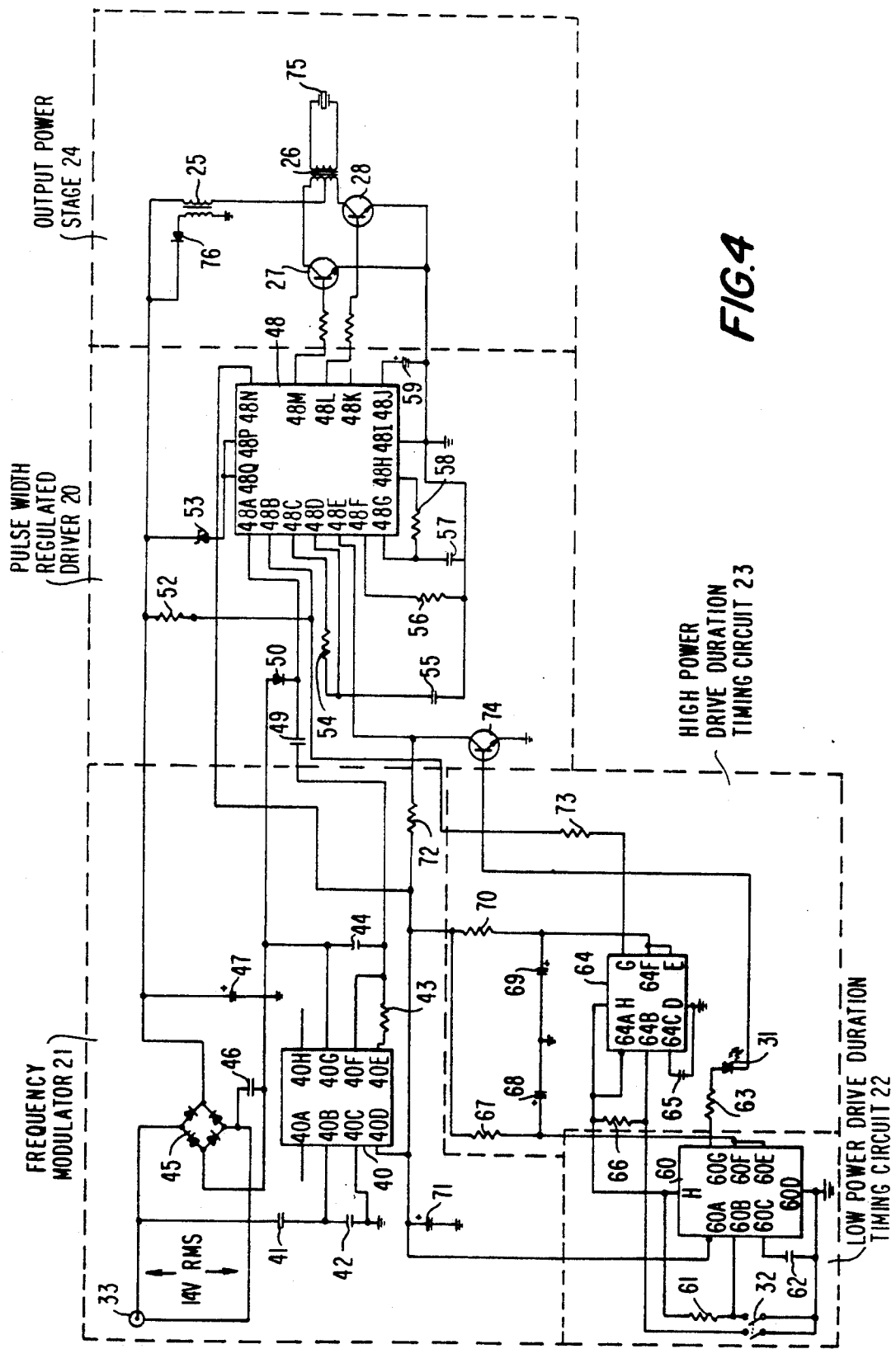
FIG. 4 is a circuit diagram of the power drive of the embodiment of FIG. 2.

As shown in FIGS. 3 and 4, the power circuit comprises a pulse width regulated driver 20 of any suitable known type controlled in frequency by the output of a frequency modulator 21 of any suitable known type and controlled in the duration of drive by a low power drive duration timing circuit 22 of any suitable known type and a high power drive duration timing circuit 23 of any suitable known type. The driver 20 has an output power stage 24 (FIGS. 3 and 4) which is a current mode, push-pull unit having an inductor 25, an output transformer 26 and a pair of bypolar transistors 27 and 28, as shown in FIG. 4.

The pulse width regulated driver 20 may, for example, be that described in Linear Integrated Circuits DATABOOK, #C500, Unitrode Corporation, 1987, UC3525A, pages 3-39 to 3-45, Application Note U-89 pages 9-4 to 9-14. The timer chips of the low and high power drive duration timing circuits 22 and 23 may, for example, be that described in Linear Databook 3, National Semiconductor Corporation, 1988 edition, #400043 Rev 1, LM555 Timer, pages 5-38 to 5-45. The output power stage 24 is preferably a current driven invention as described in Design of Solid-State Power Supplies by Eugene R. Hnatek, Second Edition, 1981, Van Nostrand Reinhold Company, pages 466 to 477.

The power circuit is electrically connected to the piezoelectric crystals 6 and 7 via electrodes 29 and 30, respectively, as shown in FIG. 2. The acoustic resonant structure 5 is thus electrically driven by a controlled level of power at its resonant frequency, which is approximately 60 kHz. This is sufficient to produce ultrasonic cavitation bubbles in the cleaning solution 13. The frequency modulation control of the pulse width regulated driver 20 causes the drive frequency to constantly change at a 120 Hz rate in order to compensate for any variations in the depth of the solution 13 in the container 4.

The high power drive duration timing circuit 23 times the high power ultrasonic drive duration for cleaning lenses and the low power drive duration timing circuit 22 times the lower power drive duration for soaking and disinfecting lenses. Upon accomplishment of its function, the low power drive duration timing circuit 22 energizes a light emitting diode or LED 31 (FIGS. 1 and 4) which is connected in the output of said timing circuit and placed at a window of the housing 1 where it is readily observable. Timing for the higher power cleaning is usually two minutes and for the total time of application of high and low ultrasonic power is usually ten minutes.

When a switch 32 in the housing 1 is depressed in initiates a timing cycle for operation of the contact lens cleaning device of the invention by causing the membrane switch 32 (FIGS. 1 and 4) of any suitable known type to close. Power is supplied to the power circuit from main 50/60 Hz utility lines via any suitable known type of input socket 33 (FIGS. 1 and 4).

Halleck, in U.S. Pat. No. 4,382,824, which issued May 10, 1983, discloses the use of a saline solution to synergistically clean and disinfect in one step at a temperature not higher than 65 degrees C., by employing the preferred values of frequency and intensity as indicated in Table IV and FIG. 3 of between 62 and 72 kHz and an intensity of 0.8 and 2 watts per ml. which will disinfect the solution in a time period of not longer than 20 minutes.

Although shown and described in what is believed to be the most practical and preferred embodiment, it is apparent that departures from the specific method and designs described and shown will suggest themselves to those skilled in the art and may be made without departing from the spirit and scope of the invention. We, therefore, do not wish to restrict ourselves to the particular construction described and illustrated, but desire to avail ourselves of all modifications that may fall within the scope of the appended claims.

We claim:

1. An ultrasonic cleaning device for cleaning an item having surfaces desired to be kept free of scratching and the like, said device comprising
    a liquid holding container having a cleaning solution therein, said container having means for holding an item in said cleaning solution;
    acoustic resonant structural means having piezoelectric components and operatively coupled to said container; and
    frequency modulated power means electrically connected to and driving said acoustic resonant structural means and providing a controlled level of ultrasonic cleaning energy, said power means including timing circuits for controlling the level of applied energy to a first determined power level for a first determined period of time followed by a second determined power level less than the first power level for a second determined period of time longer than the first period of time thereby preventing overheating and harm to said item due to excess heat or caviation.

2. An ultrasonic cleaning device as claimed in claim 1, wherein said acoustic resonant structural means comprises a pair of piezoelectric crystals, a pair of metal end sections, said crystals being sandwiched between said end sections, and means holding said crystals and said end sections in axial relation and said acoustic resonant structural means is adhered to said container.

3. An ultrasonic cleaning device as claimed in claim 1, wherein said container comprises plastic material and has a plastic lid and item holding means affixed to said lid for holding a plurality of items separately from each other in a cleaning solution in said container and permitting free flow of said solution on each of said items.

4. An ultrasonic cleaning device as claimed in claim 1, wherein said frequency modulated power means provides drive electrical energy at which said acoustic resonant structural means is driven and said drive energy has a frequency which is continually varied at 120 Hertz to compensate for variations in solution depth in said container.

5. An ultrasonic contact lens cleaning device, comprising
    a liquid holding container having a lens cleaning solution therein, said container having means for holding a lens in said cleaning solution;
    acoustic resonant structural means having piezoelectric components and operatively coupled to said container; and
    frequency modulated power means electrically connected to and driving said acoustic resonant structural means and providing a controlled level of ultrasonic cleaning energy, said power means including timing circuits for controlling the level of applied energy to a first determined power level for a first determined period of time followed by a second determined power level approximately half the first power level for a second predetermined period of time approximately three to four times longer than the first period of time thereby preventing overheating and harm to said lens due to excess heat or cavitation.

6. An ultrasonic contact lens cleaning device as claimed in claim 5, wherein said acoustic resonant structural means comprises a pair of piezoelectric crystals, a pair of metal end sections, said crystals being sandwiched between said end sections, and means holding said crystals and said end sections in axial relation and said acoustic resonant structural means is adhered to said container.

7. An ultrasonic contact lens cleaning device as claimed in claim 5, wherein said container comprises plastic material and has a plastic lid and lens holding means affixed to said lid for holding a plurality of lenses separately from each other in a cleaning solution in said container and permitting free flow of said solution on each of said lenses.

8. An ultrasonic contact lens cleaning device as claimed in claim 5, wherein said frequency modulated power means provides drive electrical energy at which said acoustic resonant structural means is driven and said drive energy has a frequency which is continually varied at 120 Hertz to compensate for variations in solution depth in said container.

9. An ultrasonic contact lens cleaning device, comprising
    a housing;
    a hemispherical cover hingedly affixed to said housing;
    a container for a lens cleaning solution mounted in said housing, said container having means for holding a lens in said cleaning solution in said container;

acoustic resonant structural means in said housing coupled to said container, said structural means having piezoelectric components; and frequency modulated power means in said housing electrically connected to and driving said acoustic resonant structural means and providing a controlled level of ultrasonic cleaning energy, said power means including timing circuits for controlling the level of applied energy to a first determined power level for a first determined period of time followed by a second determined power level less than the first power level for a second determined period of time longer than the first period of time thereby preventing overheating and harm to said lens due to excess heat or cavitation.

10. An ultrasonic contact lens cleaning device as claimed in claim 9, wherein said container has a lid and lens holding means affixed to said lid for holding a plurality of lenses separately from each other in said cleaning solution in said container while permitting free flow of said solution on each of said lenses.

11. An ultrasonic method of cleaning an item having surfaces desired to be kept free of scratching and the like, said method comprising the steps of operatively coupling acoustic resonant structural means to a liquid holding container having a cleaning solution therein;

holding item in said cleaning solution in said liquid holding container;

driving said acoustic resonant structural means with frequency modulated electrical power to provide a controlled level of ultrasonic cleaning energy;

controlling the level of energy applied to said acoustic resonant structural means to a first determined power level for a first determined period of time; and controlling a second determined power level to less than the first power level for a second determined period of time longer than the first period of time thereby preventing overheating and harm to said item due to excess heat or cavitation.

12. An ultrasonic method as claimed in claim 11, wherein said electrical power has a frequency which is continually varied at 120 Hertz to compensate for variations in solution depth in said container.

13. An ultrasonic method as claimed in claim 11, wherein said second determined power level is approximately half the first power level and said second determined period of time is approximately three to four times longer than the first period of time.

* * * * *